United States Patent [19]
Kurosaki et al.

[11] 4,189,474
[45] Feb. 19, 1980

[54] DEXTRIN HYDROXYCARBOXYLATO POLYIRON (III) OLATED COMPLEX AND PROCESS FOR THE MANUFACTURE THEREOF

[75] Inventors: Teikichi Kurosaki, Osaka; Kanzo Ohta, Yao; Hirohide Matsuura, Minoo; Katsumi Sawada, Higashi-osaka, all of Japan

[73] Assignee: Nippon Zoki Pharmaceutical Co., Ltd., Osaka, Japan

[21] Appl. No.: 755,649

[22] Filed: Dec. 30, 1976

[30] Foreign Application Priority Data

Jan. 1, 1976 [JP] Japan .................................. 51/256

[51] Int. Cl.$^2$ ..................... A61K 31/715; C08B 37/02
[52] U.S. Cl. ..................................... 424/180; 536/103; 536/113
[58] Field of Search .................. 536/103, 113; 424/180

[56] References Cited

U.S. PATENT DOCUMENTS

| | | | |
|---|---|---|---|
| 3,086,009 | 4/1963 | Zuschek et al. | 536/103 |
| 3,252,863 | 5/1966 | Lindvall et al. | 536/103 |
| 3,536,696 | 10/1970 | Alsop et al. | 536/103 |

*Primary Examiner*—Johnnie R. Brown
*Attorney, Agent, or Firm*—Pennie & Edmonds

[57] ABSTRACT

The present invention is directed to an iron complex used in treatment of iron-deficiency anemia. The complex is formed by reacting a reactive polyiron (III) olated compound with dextrin and at least one hydroxycarboxylic acid. A dextrin-hydroxycarboxylato-polyiron (III) olated complex is produced. The reaction product contains substantially no free iron. Iron concentration is between about 35 and 47%. The complex can be administered non-orally.

The compound of the subject invention has advantages over prior art compounds. Specifically, the subject complex has a high iron content, is thermally stable, and can be preserved. It may be administered intravenously without accumulating in the blood of an animal or damaging its tissue. No serious side effects result from use of the subject complex.

18 Claims, 7 Drawing Figures

———— : DEXTRIN HYDROXYCARBOXYLATO POLYIRON(III)OLATED COMPLEX
- - - - - : FERRIC IRON IONE

———: Fe ELUTION CURVE
----: DEXTRIN ELUTION CURVE

———: Fe ELUTION CURVE
----: DEXTRIN ELUTION CURVE

DEXTRIN HYDROXYCARBOXYLATO POLYIRON (III) OLATED COMPLEX AND PROCESS FOR THE MANUFACTURE THEREOF

TECHNICAL FIELD

The present invention relates to an iron complex useful in treatment of iron-deficiency anemia, more specifically, to dextrin-hydroxycarboxylato-polyiron (III) olated complex which can be administered non-orally and a process for the manufacture thereof.

BACKGROUND ART

Treatment of iron-deficiency anemia typically employs oral administration of an iron preparation, but sometimes the administration is not done orally but non-orally: when a large volume of iron has to be administered; when an orally-administered iron preparation cannot be properly absorbed; when a patient experiences side effects from oral administration of such preparations; and when iron loss due to chronic, sustained hemorrhage is greater than iron absorption resulting in loss of stored iron.

When an iron preparation is administered orally, the rate of its absorption through the intestinal canals depends on the concentration of free iron; and accordingly, free iron has a higher therapeutic effect. For this reason, a ferrous preparation which can exist as free iron in high concentration is more often used for therapeutic purposes.

Depending upon dosage, non-oral administration of free iron can bring a living thing to which it has been administered to an extremely dangerous state. Thus, strenuous efforts are being made to manufacture iron preparations with a low content of free iron. Unlike oral iron preparations, non-oral iron preparations have to meet basically different requirements: namely, adequate molecular weight; minor excretion in urine; high concentration of iron; easy availability of injection liquid, which is isotonic with the body fluid; stability of solution around neutrality; and stable storability as a solution. Thus, the non-oral iron preparations require more demanding manufacturing techniques than the oral ones to assure safety and stability.

Several patents disclose the effectiveness of complexes composed of a ferric salt, a mono- or oligosaccharide and a hydroxycarboxylic acid for treatment of iron-deficiency anemia. For example, Japanese Patent Publication Nos. SHO 40-7296 and SHO 40-17782 disclose a method of obtaining an iron preparation by reacting a ferric salt, hexytol and a mono-, di- or tribasic hydroxycarboxylic acid in the presence of a dispersion-stabilizer. This method, however, can produce only a preparation with a relatively low iron content of 15-16%; and when injected into the veins of a mouse, the preparation produces high toxicity value of $LD_{50}$ of 35 mg/kg.

Japanese Patent Publication No. SHO 46-3196 discloses a method of obtaining an iron preparation by reacting one mole of ferric hydroxide with two moles of a complex-forming agent composed of about 1.5 mole of sorbitol, about 0.4 mole of gluconic acid and 0.5 mole (as glucose) of dextrin with mean molecular weight between 500 and 1200, dextran, hydrogenated dextrin or hydrogenated dextran. The resulting iron preparation also has a low iron content between 21 and 26%. When administered to a human being, 10% of the iron administered is excreted in urine; and the value of $LD_{50}$, when intramuscularly injected into a mouse, is 380 mg/kg which means relatively high toxicity.

These saccharide-hydroxycarboxylic-ferric complexes also have the following drawbacks: with relatively low molecular weight, the complexes are likely to damage blood corpuscle, blood vessel and muscle; and solutions of the complex can be stable only at pH values far higher than those of blood and body fluid. Thus, those complexes are not useful as iron preparations that can be administered non-orally.

In the case of dextran-ferric complex, which has been available as an iron preparation for non-oral administration, it is extremely slow to decompose within an animal body. Dextran is cumulative, and when administered nonorally, it is poorly taken into the reticuloendothelial system of the body. Dextran accumulates in the blood, acts as an antigen, yielding an anti-body, and is reported as carcinogenic. Moreover, dextran is expensive. Thus it is controversial in non-oral applications.

In the case of dextrin-ferric complex, dextrin, unlike dextran, is not cumulative on account of metabolizing enzymes being present in the body, and it does not yield harmful antibodies. Having a high molecular weight, the dextrin-ferric complex is not filtered off by the kidney and is excreted in a minor amount as urine. Dextrin, however, contains a reducing group which can yield a free ferrous ion by reducing a ferric compound to a ferrous one. Moreover, the dextrin-ferric complex in a liquid phase lacks stability during prolonged storage and lacks thermal stability.

The present inventors attempted to improve the stability of iron preparations using high molecular weight dextrin, but failed to attain such a result. Only preparations having a poor curative effect and a low iron content were obtained. The manufacture of a dextrin-ferric complex having an increased iron content, having a decreased effect of the reducing group in dextrin and having a yield substantially free of ferrous ion, was tried. That resulted in an unstable complex with a decreased water retention.

DISCLOSURE OF THE INVENTION

The present invention is directed to the successful production of an iron complex, which is free from the above drawbacks. The complex is formed by reacting a reactive polyiron (III) olated compound with dextrin having a suitable molecular weight and at least one hydroxycarboxylic acid at a favorable ratio for coordinate bonding. The acid is selected from such acids as citric acid, gluconic acid, tartaric acid, malic acid or succinic acid or from an alkali salt thereof, preferably sodium citrate or potassium citrate. A dextrinhydroxycarboxylato-polyiron (III) olated complex is produced.

The present invention offers a highly stable, safe non-oral iron preparation which contains about 35 to 47% iron. The preparation contains practically no free iron, and when administered, is barely excreted in urine.

BEST MODE FOR CARRYING OUT THE INVENTION

Figure 1:
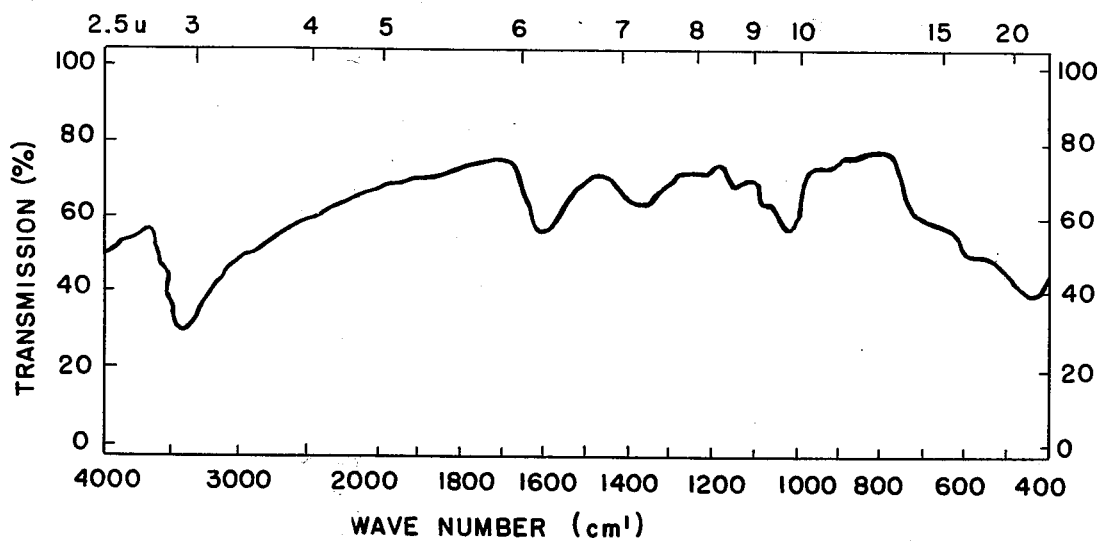
FIG. 1 illustrates infrared absorption spectra by potassium bromide tablet method of the complex of Example I.

According to the present invention, a crude solution of dextrin-hydroxycarboxylato-polyiron (III) olated complex can be obtained by mixing and heating the following substances with agitation, for about 1 to 5 hours at a temperature between 100° C. and 130° C., preferably 102° C. and 120° C., in a vessel equipped with heating and stirring means:

(1) polyiron (III) olated compound, (2) Dextrin having a mean molecular weight, calculated from the number of reducing end-group measured by SomogyiNelson method, of about 2,500 to about 10,000 preferably 3,500 to 6,000, whose 2% solution is soluble at 4° C. after 7 days without formation of a precipitate in an amount of about 0.75 to 1.60 mole (glucose residue unit) per mole of iron, hereafter dextrin.

(3) at least one hydroxycarboxylic acid selected from among citric acid, gluconic acid, tartaric acid, malic acid and succinic acid or alkali salt thereof, preferably citric acid or its sodium or potassium salt, in an amount of about 0.02 to 0.20 mole, preferably 0.05 to 0.16 mole, per mole of iron, (4) at least one alkali carbonate selected from the group consisting of sodium carbonate and potassium carbonate, and (5) water.

Alternatively, the crude solution of dextrin-hydroxycarboxylato-polyiron (III) olated complex can be obtained by the following process:

(1) heating and agitating for about 1 to 5 hours at about 100° C. to 130° C., preferably 102° C. to 120° C. in the presence of carbonic alkali carbonate, a mixture of a polyiron (III) olated compound and dextrin in an amount of about 0.75 to 1.60 mole (glucose residue unit) per mole of iron, (2) diluting the resulting solution with water and filtering it to remove unreacted substances, and (3) separating dextrin-polyiron (III) olated complex by precipitation by adding to the filtrate at least one lower alkanol selected from among methylalcohol, ethylalcohol and isopropylalcohol and then centrifuging the mixture. A purified dextrin-polyiron (III) olated complex containing alcoholic water is obtained. It is preferable to repeat the above procedure. The concentration of the lower alkanol in this process must be at least about 30% v/v. Higher alcohol concentrations lower the purity of the product.

(4) dissolving by heating with water the resulting purified dextrin-polyiron (III) olated complex containing alcoholic water as such or the resulting complex after dried it up. When using a purified dextrin-polyiron (III) olated complex containing lower alkanol water, it is desirable to distill the lower alkanol by boiling.

(5) heating and agitating that solution for about 1 to 5 hours at about 110° C. to 130° C. in a sealed vessel, after addition of about 0.02 to 0.2 mole, preferably 0.05 to 0.16 mole per mole of iron, of at least one hydroxycarboxylic acid or alkali salt thereof.

The crude solution of dextrin-hydroxycarboxylatopolyiron (III) olated complex obtained by either of the above processes is filtered and at least one lower alkanol selected from among methylalcohol, ethylalcohol and isopropylalcohol is added to the filtrate whereby the complex precipitates. The precipitate is centrifugally separated and a purified dextrin-hydroxycarboxylato-polyiron (III) olated complex is obtained. Next, that complex, containing lower alkanol water, is dried in a warm-air drying chamber or in a vacuum, and if necessary, it is crushed and then stored for subsequent preparation into a non-oral iron medication.

The above-mentioned purification process is effective to eliminate unreacted alkali salt of the hydroxycarboxylic acid, free iron, a complex with low iron content and a complex with low molecular weight. Therefore, the process of the present invention contributes to improvement in the stability and safety of the subject complex.

The subject polyiron (III) olated compound can be produced with relative ease by, for example, slowly adding an excess amount of aqueous solution of alkali carbonate to an aqueous solution of ferric chloride while thoroughly stirring the mixture at room temperature or below room temperature. The resulting suspension is washed with distilled or pure water and separated using filtration or centrifugal separation techniques. In the polyiron (III) olated compound thus obtained, it is desirable that the electolyte which hinders coordinate binding of other components and accordingly causes a decrease in the iron content be substantially eliminated. This elimination can be attained easily and more economically using the above process than by ion exchange or dialysis.

In the present invention, great significance is attached to the use and amount of hydroxycarboxylic acid or an alkaline salt thereof. Specifically, when hydroxycarboxylic acid or an alkaline salt thereof is used as component of the polyiron complex, the stability in solution phase can be remarkably improved compared with a dextrinpolyiron (III) olated complex because the end of the substance has a negative charge. The most striking improvement in the stability of the solution phase is achieved when an alkali salt of citric acid is used in an amount between 0.02 and 0.20 mole, preferably 0.05 to 0.16 mole, per mole of iron. The molecular weight of the yielded complex decreases with an increase of the amount of the reacted alkali salt of hydroxycarboxylic acid in the complex. Thus, the amount of salt can be used to adjust the molecular weight of the complex.

Moreover, the volume of dextrin in the complex of this invention has a significant bearing on the stability of a solution of the complex. Generally, an increase in the volume of dextrin and a decrease in the iron content of the material results in a greater concentration of free iron, which results in a decreased stability and safety. Large reductions in the volume of dextrin, however, are not desirable, because that causes a decrease in the water retention and in the stability of the complex.

Therefore, the present invention is characterized by use of a minor volume of dextrin to increase the iron content in the complex. Hydroxycarboxylic acid is used to offset a decrease in the hydrophilic properties of the complex. Thus, the complex of this invention should contain a dextrin concentration so that a complex having a high molecular weight can be produced without lowering the stability of the complex. This is effected by using dextrin at a concentration of about 0.75 to 1.6 moles (glucose residue unit) per mole of iron.

The dextrin-hydroxycarboxylato-polyiron (III) olated complex of the present invention is a dark brown, odorless, amorphous powder which is slightly soluble in cold water and readily soluble in hot water. Once dissolved, it can yield a stable solution which does not precipitate when cooled. This solution is stable around neutrality, and it is only slightly soluble in organic solvents such as ethanol, methanol, acetone, ether and the like.

The subject complex has a high molecular weight and has a negative charge. Its average molecular weight, as measured from the osmotic pressure, is about 140,000, and has a particular molecular weight distribution.

The iron complex produced by the present invention has the following advantages:

(1) Because iron content is high, the complex is easily formulated and stored.

(2) When intravenously administered, it can be readily taken into the bone marrow, liver, spleen and other endothelial tissues and does not accumulate in the blood, unlike a dextran ferric compound.

(3) An aqueous solution of the complex is stable around neutrality and is unlikely to damage animal tissue.

(4) Because dextrin and hydroxycarboxylic acid can be metabolized, the complex is noncumulative after administration and free from any serious side effects.

(5) High preservability and thermal stability in solution phase favour sterilization of the complex during formulation, storage and distribution.

Toxicity and pharmacological activities of the subject complex have been investigated. An acute toxicity test of dextrin-citrato-polyiron (III) olated complex using test groups of 8 male mice revealed that the value of $LD_{50}$ for the complex is about 460 mgFe/kg for intravenous administration, and over 2500 mgFe/kg for subcutaneous administration. Six male guinea pigs were also subcutaneously injected three times every other day at the belly or at the back nape with 10 mgFe/kg of the complex to sensitize the pigs. After 3 weeks, the pigs were examined for systemic anaphylaxis. A Schltz-Dale test and other tests were also carried out using the ileum of the sensitized guinea pig to determine antigenicity. The results were negative for each test.

A dextrin-citrato-polyiron (III) olated complex containing $^{59}Fe$ with an iron content of 250 mg was mixed with a 20% glucose solution and was intravenously administered to human patients of agastric iron-deficiency anemia to investigate the behavior of the iron complex. From the plasma-iron disappearance curve, the half life of iron was found to be about 29 minutes. The red cell iron utilization curve continued to rise for 14 days, and the iron utilization rate was recorded at over 70%. A body surface measurement of radioactivity showed that the distribution of $^{59}Fe$ within the body after 24 hours was the highest in the liver, followed by bone marrow and spleen. After 3 to 4 days, $^{59}Fe$ concentration was the highest in bone marrow, while it began to drop in the liver. The concentration in the heart, which represents the concentration in the blood, increased. This shows utilization by red corpuscles.

On the other hand, depending on the seriousness of the patient, one to two ampoules per day of the injection liquid (each ampoule containing 2 ml of liquid which comprises about 110 to about 145 mg (50 mg in terms of iron) of dextrin-citrato-polyiron (III) olated complex, 80 mg of sorbitol and adequate amounts of distilled water for injection) were intravenously or intra-muscularly administered 2 to 7 times per week to 55 patients of iron-deficiency anemia caused by gynecological problems. In 38 patients, hemoglobins increased by over 1.5 g/dl, by 1.0 to 1.4 g/dl in 12 patients, and by less than 1.0 g/dl in 5 patients. Thus, a significant improvement was observed in most patients. No side effects were recorded, and no symptoms of acute iron poisoning, allergy and functional lesion of liver were observed.

The complex of the present invention can be adapted for injection by dissolving it in a distilled water carrier which preferably includes an adequate volume of at least one isotonic liquid of a non-reducing type such as salt, a hexitol such as sorbitol or mannitol, and a polyhydric alcohol such as glycerin or ethylene glycol.

EXAMPLES

The following examples illustrate the invention without, however, limiting it:

EXAMPLE I 185 g of newly produced polyiron (III) olated compound (0.25 mole in terms of iron atoms), 34 g of dextrin with molecular weight of 5,000, 7.4 g of sodium citrate dihydrate and 2.8 g of anhydrous sodium carbonate together with a small amount of water were charged into an autoclave, and after being thoroughly mixed, were reacted for 2 hours at 120° C. while being agitated to yield a dark brown crude solution of dextrin-citrato-polyiron (III) olated complex. After addition of 500 ml water, the solution was filtered to remove water-insoluble substances. Into the obtained filtrate, after diluting the filtrate with water to a total volume of 1,000 ml, 640 ml of methylalcohol was added, to precipitate the complex. After standing for some time, the supernatant liquid was discarded. The sediment was separated by centrifugal force and then dissolved by heating it in a boiling bath with 350 ml of water. After being cooled, the solution was filtered through pulp, and the filtrate was diluted with water to a total volume of 600 ml. 600 ml of ethanol was added to this solution. After left standing for some time, the supernatant liquid was discarded and by centrifugal separation, a cake of pure dextrin-citrato-polyiron (III) olated complex containing ethylalcoholic water was recovered. The precipitate was dried at room temperature on calcium chloride under vacuum. The dried substance was crushed to 26.3 g of dark brown powder of dextrin-citrato-polyiron (III) olated complex. The iron content was 43.5%, and the yield (in terms of iron) was 81.4%.

EXAMPLE II 78 g of newly produced polyiron (III) olated compound (5.6 g in terms of iron), 19.5 g of dextrin with molecular weight 5,100, 2.9 g (0.01 mole) of sodium citrate dihydrate, 1.2 g of anhydrous sodium carbonate and a small amount of water were reacted under agitation for 3 hours at 115° C. in a glass autoclave to yield a concentrated solution of dextrin-citrato-polyiron (III) olated complex. After addition of 200 ml of water, the solution was filtered. The filtrate was diluted with water to a volume of 400 ml. Then, 285 ml of methylalcohol was added to precipitate the complex. After centrifugal separation, the precipitate was heated with 150 ml of water to dissolve it. The solution was cooled and filtered through pulp. The filtrate was diluted with water to a volume of 230 ml. With addition of 250 ml of ethylalcohol, the complex was precipitated and then centrifugally separated. The sediment was dried under vacuum on calcium chloride. 10.4 g of dextrin-citrato-polyiron (III) olated complex were produced having an iron content of 43.0%. The yield (in terms of iron) was 80.4%.

EXAMPLE III

Using 1.0 g (0.01 mole) of sodium glycolate instead of sodium citrate dihydrate, and in the manner described in Example II, 11.9 g of dextrin-glycolato-polyiron (III) olated complex was produced having an iron content of 38.7% and yield (in terms of iron) of 82.1%.

EXAMPLE IV

Using 2.2 g (0.01 mole) of sodium gluconate instead of sodium citrate dihydrate and in the manner described in Example II, 10.9 g of dextrin-gluconato-polyiron (III) olated complex was obtained having an iron content of 42.8% and yield (in terms of iron) of 83.9%.

EXAMPLE V

Using 2.3 g (0.01 mole) of sodium tartrate dihydrate instead of sodium citrate dihydrate, and in the manner set forth in Example II, 11.0 g of dextrin-tartrato-polyiron (II) olated complex was produced with iron content of 42.1% and yield (in terms of iron) of 82.1%.

EXAMPLE VI

Using 1.8 g (0.01 mole) of sodium malate instead of sodium citrate dihydrate and in the same way described in Example II, 10.8 g of dextrin-malato-polyiron (III) olated complex was obtained having an iron content of 39.3% and yield (in terms of iron) of 75.0%.

THERMAL STABILITY TEST

Aqueous solutions having an iron concentration of 25 mg/ml of dextrin-citrato-polyiron (III) olated complex obtained as in Example II and dextrin-polyiron (III) olated complex obtained as in Example II without addition of sodium citrate dihydrate were charged into ampoules. The ampoules were then heated to 100° C. to test thermal stability. Every 25 hours the samples were compared regarding appearance and cataphoretic test for evaluation of thermal stability.

The comparison showed that the appearance of the sample of dextrin-citrato-polyiron (III) olated complex did not change even after 200 hours and behaved well in a cataphoretic test too. The sample of dextrin-polyiron (III) olated complex, without sodium citrate, gelled after 25 hours, and a placing point residue was observed in a cataphoretic test.

Similar tests carried out with alkali salts of hydroxycarboxylic acids other than sodium citrate revealed that these salts, though somewhat inferior to sodium citrate, are significantly better in thermal stability than dextrinpolyiron (III) olated complex.

All thermal stability tests mentioned hereafter were carried out in the manner described above.

EXAMPLES VII–XI

Five experiments were conducted. The experiments differed only in the quantity of sodium citrate dihydrate reacted. Those quantities were: 0.01, 0.02, 0.10, 0.15 and 0.3 mole of sodium citrate dihydrate per mole of iron.

An amount of sodium citrate dihydrate, 146 g (0.2 mole in terms of iron) of newly produced polyiron (III) olated compound, 42 g of dextrin with molecular weight 5,600 and 2.3 g of anhydrous sodium carbonate were reacted under identical conditions in substantially the same manner as in Example I. Dextrin-citrato-polyiron (III) olated complexes formed were evaluated regarding yield, iron content and thermal stability, the results being summarized in Table I.

TABLE I

| Example | Iron: Sodium citrate (mole ratio) | Yield % | Iron Content % | Observations |
|---|---|---|---|---|
| VII | 1 : 0.01 | Cal.84 | 38.1 | Gel after 125 hrs; placing point residue recognized in cataphoretic test |
| VIII | 1 : 0.02 | 85 | 37.5 | No change in appearance after 200 hrs; slight tailings recognized in cataphoretic test |
| IX | 1 : 0.10 | 82 | 39.8 | No change in appearance after 200 hrs; results of cataphoretic test good |
| X | 1 : 0.15 | 80 | 41.8 | Same results as in Example IX |
| XI* | 1 : 0.30 | 58 | 42.3 | Same results as in Example IX |

*The complex of Example XI is inferior to other dextrin-citrato-polyiron (III) olated complexes, because it has a high pH, a high osmotic and a low molecular weight

EXAMPLE XII 158 g of newly produced polyiron (III) olated compound (0.2 mole in terms of iron), 32.1 g of dextrin with molecular weight 3,800 and 2.0 g of anhydrous sodium carbonate, and a small quantity of water, were heated and agitated in an oil bath. The temperature was maintained at about 102° C. so that the contents slowly refluxed. After 2 hours, the brown reaction mixture turned into a dark brown homogeneous solution, which was a concentrated solution of dextrin-polyiron (III) olated complex. That solution was diluted with 400 ml of water, cooled and filtered to remove minor amounts of insoluble, unreacted substances. The filtrate was diluted with water to a total volume of 800 ml; then 520 ml of methylalcohol was added to separate the sediment. 600 ml of water was added to the sediment, and the mixture was dissolved by heating and agitating it in a boiling bath. After being cooled, the solution was filtered through pulp. The filtrate was diluted with water to a volume of 700 ml; and then, 880 ml of methylalcohol was added to precipitate dextrin-polyiron (III) olated complex. After standing, the supernatant liquid was removed; and the precipitate was centrifugally separated to yield a cake of pure dextrinpolyiron (III) olated complex containing methylalcoholic water. 260 ml of water was added to the complex. The mixture was heated and agitated, and methylalcohol was evaporated. When cool, the solution was filtered and diluted with water to a volume of 400 ml. A sample of this solution was taken for quantitative determination of iron, the yield being 89.6% in terms of iron.

The solution was charged into a simple autoclave and reacted for 2 hours at 120° C. after addition of 0.95 g of sodium citrate dihydrate. When cool, the reaction solution was filtered through a silk cloth, and the filtrate was diluted with water to a total volume of 400 ml. Dextrincitrato-polyiron (III) olated complex was precipitated after the addition of 290 ml of ethylalcohol. That complex, containing ethylalcoholic water, was dried at room temperature under vacuum in the presence of calcium chloride. The dried substance was crushed to produce a dark brown powder consisting of 18.8 g of dextrin-citrato-polyiron (III) olated complex. The iron content was 46.5%, and the yield was (in terms of iron) 77.7%.

EXAMPLE XIII 1072 g of newly produced polyiron (III) olated compound (1.4 mole in terms of iron), 280 g of dextrin with molecular weight 5,300, 15.7 g of anhydrous sodim carbonate, and 120 ml of water were charged into a reaction vessel with a reflux condenser. After stirring the solution for 4 hours at 103° C., dextrin-polyiron (III) olated complex was formed. 280 ml of water was added to the complex and that solution was filtered through pulp. The filtrate was diluted with water to a total volume of 5,600 ml. 3,800 ml of methylalcohol was added to precipitate the complex. It was separated by centrifugation. The sediment was heated and dissolved in 4,200 ml of water. When cool, it was again filtered through pulp. The filtrate was diluted with water to a total volume of 5,000 ml. 6,300 ml of methylalcohol was added to it to precipitate the complex. It was separated, heated and dissolved in 2,100 ml of water. Methylalcohol was evaporated. The solution was diluted with water to make 2,800 ml solution of dextrin-polyiron (III) olated complex. The yield was (in terms of iron) 92.2%.

400 ml (10.3 g in terms of iron) of a solution of dextrin-polyiron (III) olated complex and 5.4 g of sodium citrate dihydrate were reacted in the manner described in Example XII to form 23.7 g of dextrin-citrato-polyiron (III) olated complex which had an iron content of 39.6% and a yield (in terms of iron) of 83.9%.

Examples XIV to XVIII iterated the procedure of Example XII. In each example, 400 ml (10.3 g in terms of iron) of dextrin-polyiron (III) olated complex solution from Example XIII was reacted with a sodium salt of a hydroxycarboxylic acid.

EXAMPLE XIV 400 ml of the solution from Example XIII and 1.81 g of sodium glycolate were reacted in the manner noted above to produce 23.8 g of dextrin-glycolato-polyiron (III) olated complex with an iron content of 38.8% and yield of 82.1%.

EXAMPLE XV 400 ml of the complex obtained in Example XIII and 4.0 g of sodium gluconate were reacted to form 24.0 g of dextrin-gluconato-polyiron (III) olated complex having an iron content of 39.8% and yield (in terms of iron) of 85.7%.

EXAMPLE XVI 400 ml of the solution from Example XIII and 5.0 g of sodium succinate hexahydrate were reacted to produce 24.5 g of dextrin-succinato-polyiron (III) olated complex with an iron content of 38.2% and yield (in terms of iron) of 83.9%.

EXAMPLE XVII 400 ml of the complex from Example XIII and 4.2 g of sodium tartrate dihydrate were reacted to form 24.3 g of dextrin-tartrato-polyiron (III) olated complex having an iron content of 38.2% and yield (in terms of iron) of 83.0%.

EXAMPLE XVIII 400 ml of the complex obtained in Example XIII and 3.3 g of sodium malate were reacted to produce 24.2 g of dextrin-malato-polyiron (III) olated complex with iron content of 39.0% and yield (in terms of iron) of 83.9%.

THERMAL STABILITY TEST

Dextrin-polyiron (III) olated complex solution, the intermediate product, and dextrin-citrato-polyiron (III) olated complex—the end product formed in Example XIII were evaluated for thermal stability.

An ampoule preparation of dextrin-polyiron (III) olated complex formed without addition of citric acid gelled after being heated for 25 hours at 100° C. and left placing point residue in a cataphoretic test. However, an ampoule preparation of dextrin-citrato-polyiron (III) olated complex did not change its appearance even after being heated for 200 hours at 100° C. and had good results in a cataphoretic test.

Similar thermal stability evaluations with the compounds produced in Examples XIV to XVIII showed that those compounds, although somewhat inferior to dextrin-citrato-polyiron (III) olated complex, have a significantly better thermal stability than a dextrin-polyiron (III) olated complex.

EXAMPLES XIX–XXIII 907 g of newly produced polyiron (III) olated compound (1.2 moles in terms of iron), 240 g of dextrin having a molecular weight of 5,000, and 13.5 g of anhydrous sodium carbonate were reacted in the manner described in Example XIII to form 2,400 ml of a solution of dextrin-polyiron (III) olated complex. Dextrin-citrato-polyiron (III) olated complexes obtained by reacting each 0.01, 0.05, 0.10, 0.15 and 0.50 mole per mole of iron of sodium citrate dihydrate with 400 ml (10.25 g in terms of iron) of the above solution were evaluated for iron content, yield (on an iron basis) and thermal stability. The results of those reactions are tabulated in Table II.

TABLE II

| Example | Iron: Sodium Citrate (mole ratio) | Iron Content % | Yield % | Observations |
|---|---|---|---|---|
| XIX | 1 : 0.01 | 40.5 | 88.4 | Precipitates after 150 hrs; tailings recognized in cataphoretic test |
| XX | 1 : 0.05 | 40.1 | 84.8 | No change in appearance after 200 hrs; good results from cataphoretic test. |
| XXI | 1 : 0.10 | 40.6 | 85.7 | Identical to Example XX. |
| XXII | 1 : 0.15 | 39.5 | 82.1 | Identical to Example XX. |
| XXIII* | 1 : 0.50 | 37.1 | 72.3 | Identical to |

TABLE II-continued

| Example | Iron: Sodium Citrate (mole ratio) | Iron Content % | Yield % | Observations |
|---------|-----------------------------------|----------------|---------|--------------|
|         |                                   |                |         | Example XX.  |

*Complex of Example XXIII, with higher pH and osmotic pressure values and a lower molecular weight, was inferior to other dextrin-citrato-polyiron III) olated complexes.

The complex according to the present invention is formulated so that a hydrophobic polyiron (III) olated chain has changed, as a result of coordinate bonding with hydrophilic dextrin and hydroxycarboxylic acid, to a dextrinhydroxycarboxylato-polyiron (III) olated complex which is stable and dispersible in water. The complex has a high molecular weight with a particular molecular weight distribution and contains a small amount of free dextrin.

Quantitative analysis, residue analysis, infrared absorption spectra, average molecular weight, particle size distribution, cataphoresis, thin layer chromatography, intrinsic viscosity, polarography, gel filtration and other criteria of the subject complexes were determined. Procedures are described below:

a. Quantitative Analysis

Conventional analysis techniques were used to determine carbon and hydrogen content. Iron content was determined by decomposing samples in hydrochloric acid with their subsequent reduction with zinc powder to ferrous ions. Iron concentration was measured by an oxidation reduction method using ammonium cerium (IV) sulfate and using an o-phenanthroline reagent as an indicator. Sodium was analyzed using flame photometry. The results of the analyses are tabulated in Table III.

TABLE III

| Example | C % | H % | Fe % | Na % |
|---------|-----|-----|------|------|
| I       | 14.4 | 2.4 | 43.5 | 2.1 |
| XII     | 12.7 | 2.1 | 46.5 | 0.7 |
| XXI     | 16.4 | 2.6 | 40.6 | 2.2 | b. Residue Analysis

The concentration of polyiron (III) olated residue $[FeOOH]_n$ was calculated from the iron concentration determined above.

Dextrin residue $[C_6H_{10}O_5]_m$ and free dextrin $[C_6H_{10}O_5]_1$ concentrations were determined by hydrolyzing samples with hydrochloric acid to convert dextrin residue to glucose. Free dextrin was quantitatively determined by Bertrand's method. Those results were converted to dextrin volume, i.e., the total dextrin content. The free dextrin content was determined utilizing the fact that the complex portion of the compound was negatively charged. That portion was coprecipitated using solution of methylglycolchitosan, a positively charged colloidal titration reagent. Excess methylglycolchitosan was precipitated with addition of a solution of potassium polyvinyl sulphate, a negatively charged colloidal titration reagent. Free dextrin remaining in the supernatant liquid was hydrolyzed with hydrochloric acid to convert it to glucose. The results of a quantitative determination by Bertrand's method were converted to dextrin volume. The difference between total dextrin concentration and free dextrin concentration equals dextrin residue concentration.

Citric acid residue $[C_6H_5O_7]$ was hydrolyzed in 6N hydrochloric acid and then passed through a column filled with strongly acidic ion exchange resin, Amberlite IR-120, which is a sulfonated copolymer of styrene and a minor proportion of divinyl benzene, to remove iron, which hinders this measurement. The effluent was concentrated to a dry solid, which was dissolved in ethanol-water. That solution was then introduced into a cell for conductometric titration. That titration was carried out using a 0.1N NaOH solution. The citric acid residue was calculated from the volume of 0.1N NaOH consumed.

The results of these measurements are summarized in Table IV.

TABLE IV

| Residue (formula) | Example I | Example XII | Example XXI |
|-------------------|-----------|-------------|-------------|
| Polyiron (III) olated residue $(FeOOH)_n$ | 69.3% | 74.0% | 64.6% |
| Dextrin residue $(C_6H_{10}O_5)_m$ | 13.4% | 17.2% | 15.2% |
| Citric acid residue $(C_6H_5O_7)$ | 12.9% | 2.8% | 13.3% |
| Free dextrin residue $(C_6H_{10}O_5)_1$ | 8.0% | 8.3% | 10.3% | c. Infrared Spectrum

Analysis was done by the potassium bromide tablet method using an I R spectrophotometer (Hitachi-made Model EPI-G3). The infrared absorption spectra of all samples agreed with one another. The infrared absorption spectra of the complex of Example I and the characteristics of each absorption are shown in FIG. 1 and tabulated in Table V.

TABLE V

| Absorbed wave number | Characteristics | Remarks |
|----------------------|-----------------|---------|
| $3400^{cm-1}$ | strong absorption due to stretching vibration of associated OH | Attributed to dextrin residue, polyiron (III) olated compound residue and citric acid residue |
| $2900^{cm-1}$ | weak absorption due to stretching vibration of $-CH_2-$ | Attributed to dextrin residue and citric acid residue |
| $1600^{cm-1}$ | broad, strong absorption due to stretching vibration of carboxylic $acid\ O\diagdown \overset{O}{\underset{O}{\diagup}}$ | Attributed to citric acid residue |
| $1380^{cm-1}$ | broad, strong absorption due to stretching vibration of carboxylic acid C-O and due to deformation vibration of O-H | Attributed to citric acid residue |
| $1150^{cm-1}$ | weak absorption due to stretching vibration of C-O-C | Attributed to dextrin residue |
| $1080^{cm-1}$ | weak absorption due to stretching vibration of secondary OH | Attributed to dextrin citric acid residue |
| $1020^{cm-1}$ | broad, strong absorption due to stretching vibration of primary OH | Attributed to dextrin residue |
| $700^{cm-1}$ | absorption due to deformation vibration of OH | Attributed to polyiron (III) olated compound residue |

The results in FIG. 1 and Table V support the theory that complexes according to the present invention, contain a coordinate bond of polyiron (III) olated complex with dextrin and citric acid.

d. Average Molecular Weight

The relation between the concentration (C) and the osmotic pressure ($\pi$) of the complexes of Examples I and XXI was determined using a high-speed membrane osmometer. Average molecular weight ($\overline{Mn}$) was calculated from the formula $\overline{Mn} = RT(\pi/C)_{c=o}$ (wherein R=84.71 cm water column/deg mol; T=absolute temperature of system). As a basis for comparison, the molecular weight of a complex of the present invention, from which free dextrin had been substantially eliminated by ultrafiltration, was calculated to be $2.34 \times 10^5$.

The results of the above measurements and calculations are summarized in Table VI.

TABLE VI

| Example | $\overline{Mn}$ |
|---|---|
| I | $1.4 \times 10^5$ |
| XXI | $1.3 \times 10^5$ | e. Particle Size Distribution

Three aqueous solutions of the complexes of Examples I, XII and XXI having a concentration of 6% w/v were filtered through ultrafiltering membranes of different porosities. The iron concentration of the filtrate was measured by colorimetry using o-phenanthroline; and the particle size distribution of each sample was determined from the rate of filtration of iron. The particle size distribution of each aqueous sample was about 0.03 to 0.1$\mu$, and about 90% of the particle size ranged from about 0.05 to 0.08$\mu$.

f. Cataphoresis

Cellulose acetate membranes (5×6 cm) were dipped in phosphoric buffer solutions having the following pH values:

5.7, 6.0, 6.5, 7.0, 7.5 and 8.0. Excess solution was removed by putting the membranes between filtering papers. Each of these membranes was attached to a cataphoretic cell filled with a phosphoric buffer solution having the same pH as the solution in which the membrane was dipped. A 6% w/v solution of each sample was deposited on the membrane, and a current of 90 V was passed through it for 40 minutes. The migration of a brown spot of the sample was observed. All samples migrated toward the anode; the migration distances are listed in Table VII.

TABLE VII

| Example | | pH of buffer Solution | | | | |
|---|---|---|---|---|---|---|
| | | 5.7 | 6.0 | 6.5 | 7.0 | 7.5 | 8.0 |
| Migration distance (mm) | I | 11 | 9 | 10 | 11 | 10 | 10 |
| | XII | 9 | 8 | 9 | 10 | 8 | 9 |
| | XXI | 10 | 10 | 10 | 11 | 9 | 10 |

No free iron was present because after the addition of a sodium primary phosphate, a light-yellow iron phosphate (FePO$_4$) was not formed.

g. Thin Layer Chromatography (TLC)

The complex of Example I was spotted on a TLC plate (5×20 cm) of a sintered silicagel-glass powder and develped using the following three developing solvents: (I) n-butanol:aceton:water (4:5:1); (II) ethyl acetate:glacial acetic acid:water (3:1:1); and (III) ethanol:water:aqueous ammonia (25:3:4). Then a color reaction was caused using a potassium ferrocyanide reagent and a mixed solution of potassium bichromate and sulfuric acid. The Rf value was measured. Because the complex of the present invention has a high molecular weight, the spot did not migrate. Neither free citric acid, sodium citrate nor free glucose were detected.

h. Intrinsic Viscosity

Solutions having different concentrations were prepared from the products of Examples I, XII and XXI. The specific gravities of each solution and water were measured at 30° C.±0.1° C. using a Sprengel-Ostwald pycnometer. Flow out time was measured at 30° C.±0.1° C. using Ubbelohde's capillary viscosimeter.

$$\text{Intrinsic viscosity } (\eta) = \lim_{c \to 0} \eta sp/c$$

was determined by extrapolation ($\eta$sp:specific viscosity; c: solution concentration). Intrinsic viscosity ($\eta$) of each solution is listed in Table VIII.

TABLE VIII

| Example | ($\eta$) |
|---|---|
| I | 0.049 |
| XII | 0.050 |
| XXI | 0.052 | i. Polarography

Figure 2:
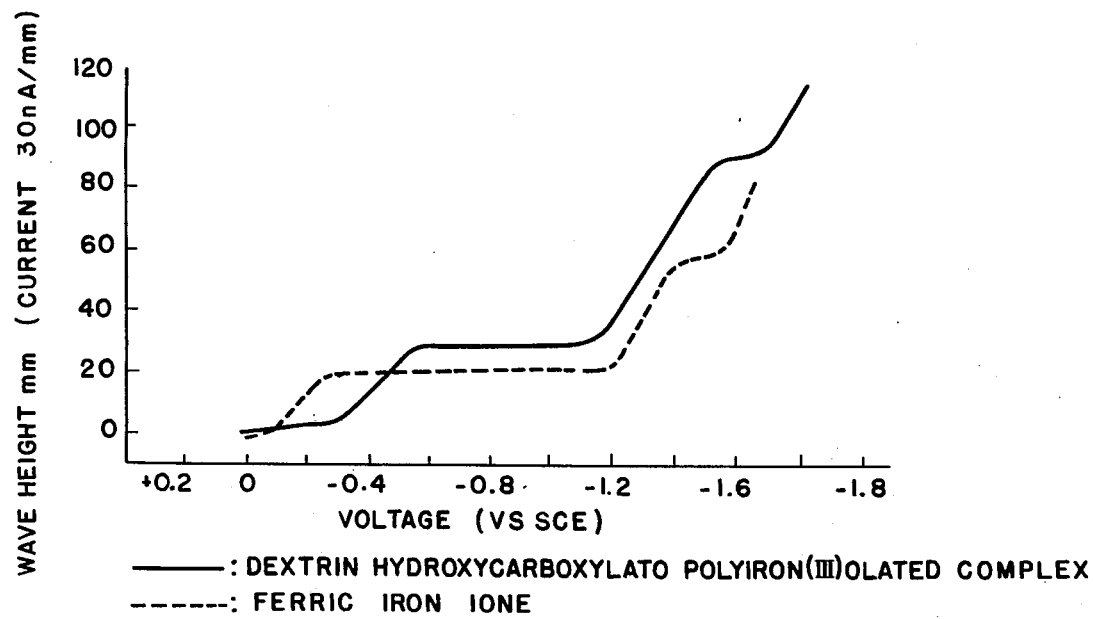
FIG. 2 is a rough figure of a polarogram of the complex of Example I at pH 5.45 using Walpole's buffer solution.

In accordance with JIS-KO111, 5 ml of supporting electrolyte (Walpole's buffer solution pH 3.50, 4.50, 5.45) was deposited in an electrolysis vessel, to which was added 20 $\mu$l of sample solution (60.0 mg/ml, Ca. 25 mgFe/ml) or a 5 $\mu$l solution of ammonium ferric sulfate (25 mgFe/ml) as a ferric ion source. The vessel was maintained at 25° C. and, a nitrogen stream was supplied for about 15 minutes to eliminate dissolved oxygen and prepare electrolyte solutions. These solutions were submitted to DC polarography under the following conditions: 60 cm Hg; current sensitivity 30 nA/mm; damping 5; and saturated calomel electrode standard (vsSCE). From a polarogram, the half-wave potential (E ½) and wave height (i) were measured. Values for half-wave potential and for wave height of the complex of Example I and of the ferric ion are tabulated in Table IX. The polarogram is illustrated in FIG. 2.

TABLE IX

| | | Electrolyte | | | | |
|---|---|---|---|---|---|---|
| | | Iron concen- | First wave | | Second wave | |
| | PH | tration | E1/2(V) | i$_1$(mm) | E1/2(V) | i$_2$(mm) |
| Example I | 3.50 | 104.4 $\mu$g/ml | −0.21 | 28.5 | −1.29 | 57.0 |
| | 4.50 | | −0.30 | 29.5 | −1.31 | 60.0 |
| | 5.45 | | −0.39 | 29.0 | −1.33 | 61.5 |
| Ferric ion | 3.50 | 25.0 $\mu$g/ml | 0.07 | 29.0 | −1.29 | 58.0 |
| | 4.50 | | 0.05 | 30.0 | −1.30 | 60.0 |
| | 5.45 | | −0.15 | 19.5 | −1.31 | 39.0 |

These data show that the complex of the present invention is stable and has a half-wave potential that is more negative than that of ferric ion. Its wave height per unit iron concentration of electrolyte is about ¼ of that of ferric ion, probably because it is a high molecular weight complex. No wave was recognized in the half-wave potential corresponding to the first wave of ferric ion in the polarogram of the sample. Thus, the ferric ion was absent.

j. Gel Filtration

Gel filtration of complexes from Examples I and XXI was done under the conditions noted below and for each eluate partition. Quantitative measurements of iron and dextrin were made.

| Sample deposit: | 6.00 mg, gel 40 × 2.5 cm | Sephalose 6B, column |
|---|---|---|
| Buffer solution: | 0.05m citric acid buffer solution (pH 6.0), volume of each partition 5 ml | |

Figure 3A:
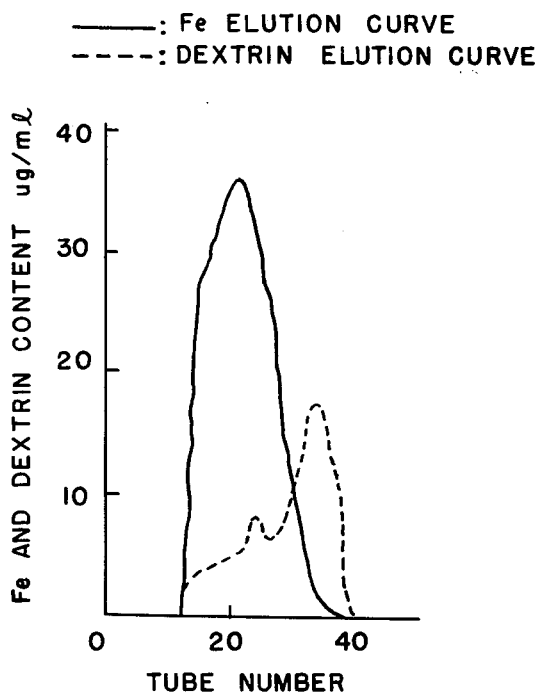
FIGS. 3A and 3B illustrate elution curves in gel filtration of the complexes of Examples I and XXI, respectively.
Figure 3B:
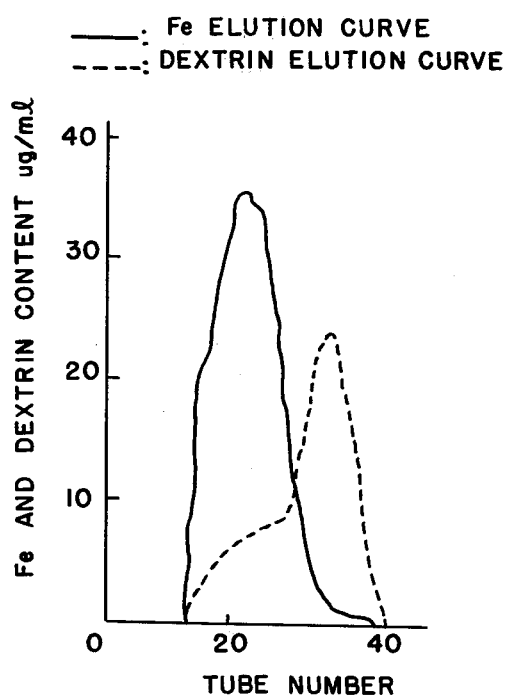

The results are summarized in FIGS. 3 A and B.

k. Stability Test

A sample, containing 5 g of iron, of the complex of Example I was diluted with 80 ml of water, and the mixture was heated in a boiling bath. When cool, the solution was diluted with water to a volume of 100 ml. This solution was used as the concentrated sample solution of 50 mgFe/ml. 10 ml of that solution was diluted with water to a volume of 20 ml, and the diluted solution was designated as sample I. Four more 10 ml samples were taken. 0.1 g, 0.2 g, 0.4 g and 0.8 g of dry dextrin was added to each sample. The samples were diluted with water to a volume of 20 ml. They were designated samples II, III, IV and V, respectively. The dextrin concentration in each sample solution and iron content in each preparation are listed in Table X.

TABLE X

| | EXAMPLE I | |
|---|---|---|
| Sample | Total dextrin concentration (mg/ml) | Iron content in preparation % |
| I | 13 | 44 |
| II | 18 | 40 |
| III | 23 | 37 |
| IV | 33 | 32 |
| V | 53 | 26 |

Figure 4:
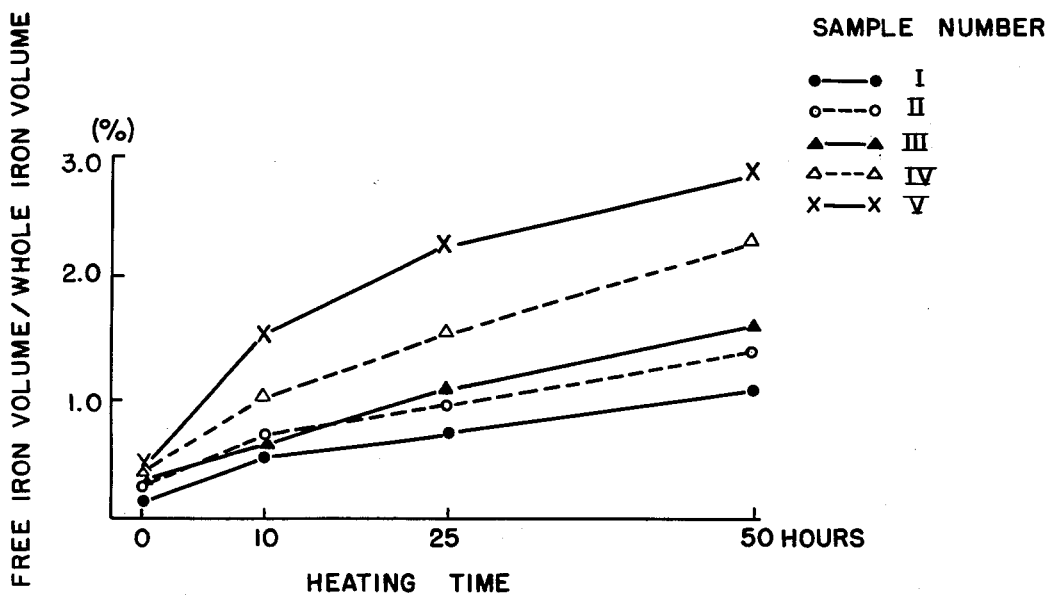
FIG. 4 illustrates the relation between heating time and free iron content of a sample solution prepared from the complex of Example I.

Each sample solution was sealed in an ampoule and was heated in a boiling bath for 0, 1, 3, 6, 10, 25 and 50 hours. Thereafter, the volume of free iron was measured. The results are summarized in FIG. 4.

l. Dextrin-citric acid-ferric ion (ultrafiltration)

Figure 5:
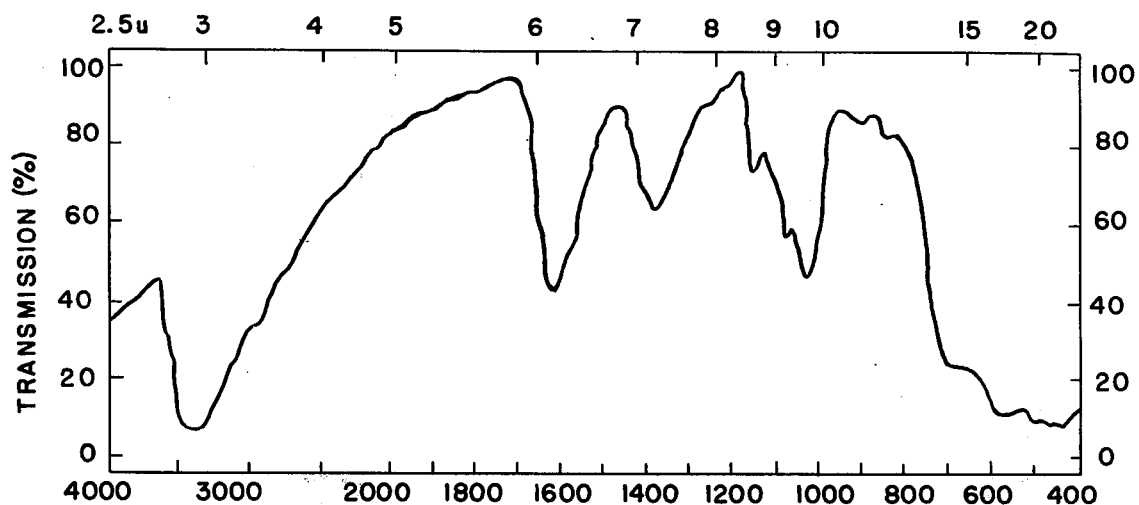
FIG. 5 illustrates infrared absorption spectra of the complex of Example XXI as untrafiltered.
Figure 6:
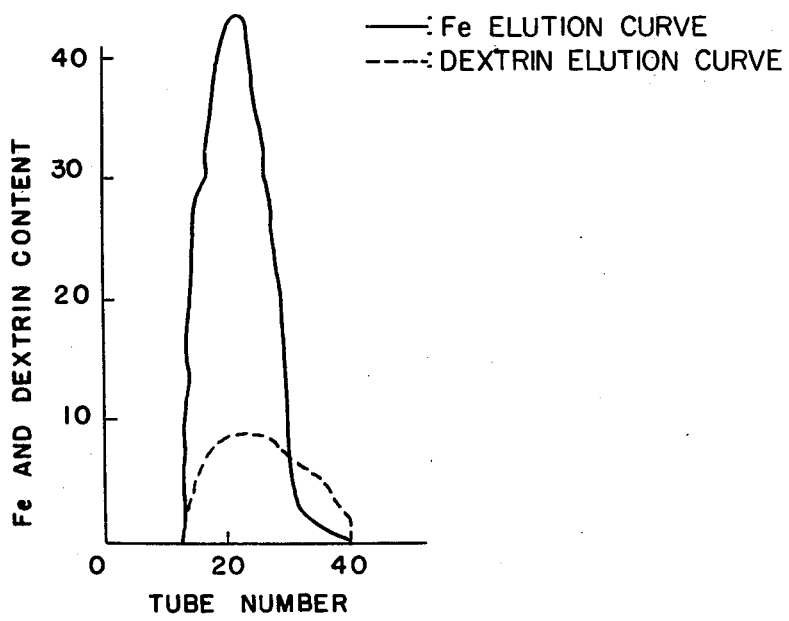
FIG. 6 illustrates the elution curve in gel filtration of this complex.

The appearance and solubility, iron content, dextrin content, infrared absorption spectra and gel filtration curve of a sample obtained by ultrafiltration of an aqueous solution of the complex of Example XII were investigated. The results are listed in Table XI. Infrared absorption spectra and gel filtration curves are illustrated in FIGS. 5 and 6, respectively.

TABLE XI

| Items investigated | Description | Remarks |
|---|---|---|
| Appearance and solubility | Dark brown odorless amorphous powder; sparingly soluble in cold water; easily soluble in hot water. Scarcely soluble in ethanol, methanol, acetone and ether. Easily soluble in mineral acids | |
| Iron content | 48.4% | |
| Dextrin content | 15.2% | |
| | 3400cm$^{-1}$ strong absorption due to stretching vibration of associated OH | Attributed to dextrin residue, citric acid residue, and polyiron (III) olated compound residue |

TABLE XI-continued

| Items investigated | Description | Remarks |
|---|---|---|
| Infrared absorption spectra attribution | 1620cm$^{-1}$ broad, strong absorption due to stretching vibration of carboxylic acid | Attributed to citric residue |
| | 1380cm$^{-1}$ broad, strong absorption due to stretching vibration of carboxylic acid C—O and due to deformation vibration of OH | Attributed to citric acid residue |
| | 1150 cm$^{-1}$ weak absorption due to stretching vibration of C—O—C | Attributed to dextrin residue |
| | 1080cm$^{-1}$ weak absorption due to stretching vibration of secondary OH | Attributed to dextrin citric acid residue |
| | 1020cm$^{-1}$ broad, strong absorption due to stretching vibration of primary OH | Attributed to dextrin residue |
| | 700cm$^{-1}$ strong absorption due to deformation vibration of OH | Attributed to polyiron (III) olated compound residue |

It is not intended to limit the present invention to the specific embodiments described above. Other changes may be made in the product and the process specifically described herein without departing from the scope and teachings of the present invention, and it is intended to encompass all other embodiments, alternatives and modifications consistent with the invention.

We claim:

1. Dextrin-citrato-polyiron (III) olated complex.

2. A dextrin-citrato polyiron (III) olated complex comprising a dark brown, odorless, amorphous powder which hardly dissolves in organic solvents such as ethanol, methanol, acetone or ether, slowly dissolves in cold water, easily dissolves in hot water, and once dissolved, yields a stable solution which does not precipitate even when cooled; a composition of about 14.4% carbon, about 2.4% hydrogen and about 43.5% iron, a residue composition of about 69.3% polyiron (III) residue, about 13.4% dextrin residue [$C_6H_5O_7$], about 12.9% citric acid residue [$C_6H_5O_7$] and about 8.0% free dextrin; an average molecular weight of about $1.4 \times 10^5$; by an intrinsic viscosity of about 0.049; a particle size distribution in a liquid phase between about 0.03 and 0.1$\mu$ with 90% being between about 0.05 and 0.08$\mu$; and an infrared absorption spectra:

3400 cm$^{-1}$ (OH), 2900 cm$^{-1}$ ($CH_2$);
1600 cm$^{-1}$ (O=C=O), 1380 cm$^{-1}$ (CO,OH);
1150 cm$^{-1}$ (C—O—C), 1080 cm$^{-1}$ (OH);
1020 cm$^{-1}$ (OH) and 700 cm$^{-1}$ (OH).

3. A dextrin-citrato-polyiron (III) olated complex comprising a dark brown, odorless, amorphous powder which hardly dissolves in organic solvents such as ethanol, methanol, acetone or ether, slowly dissolves in cold water, easily dissolves in hot water, and once dissolved, yields a stable solution which does not precipitate even when cooled; and an iron content of about 46.5%, a dextrin content of about 15.2%, an intrinsic viscosity of about 0.050, and an infrared absorption spectra:

3400 cm$^{-1}$ (OH), 1620 cm$^{-1}$ (O=C=O);

1380 cm$^{-1}$ (CO,OH), 1150 cm$^{-1}$ (C—O—C); 1080 cm$^{-1}$ (OH), 1020 cm$^{-1}$ (OH); and 700 cm$^{-1}$ (OH).

4. The dextrin-citrato-polyiron (III) olated complex of claim 2 wherein its aqueous solution, has a concentration of 25 mgFe/ml, does not gel nor does its cataphoresis change after heating for 200 hours at 100° C.

5. A non-oral pharmaceutical composition for treating iron-deficiency anemia which contains a pharmaceutically acceptable carrier and dextrin-citrato-polyiron (III) olated complex as defined in claim 2.

6. A method for treating iron-deficiency anemia in animals which comprises injecting a dosage amount of the pharmaceutical composition of claim 5 in an animal in need of such treatment.

7. A method of claim 6 wherein the dosage contains an isotonic solution.

8. A method of claim 7 wherein the isotonic solution contains sorbitol.

9. A method for manufacturing dextrin-hydroxycarboxylato-polyiron (III) olated complex which comprises reacting a polyiron (III) olated compound with dextrin and citric acid, gluconic acid, tartaric acid, malic acid or succinic acid, or alkali salts thereof between about 100° C. and 130° C. in the presence of alkali carbonate, and recovering a dextrin-hydroxycarboxylato-polyiron (III) olated complex.

10. The method of claim 9 in which the reaction temperature is between 102° and 120° C.

11. The method of claim 9 wherein the average molecular weight of dextrin is between about 2,500 and 10,000.

12. The method of claim 9 wherein the average molecular weight is between 3,500 and 6,000.

13. The method of claim 9 wherein dextrin has a 2% solubility at 4° C. after 7 days without formation of a precipitate.

14. The method of claim 9 wherein dextrin is used in an amount between about 0.75 and 1.60 mole glucose residue unit per mole of iron.

15. The method of claim 9 wherein the hydroxycarboxylic acid or alkali salt thereof is used in an amount between about 0.02 and 0.20 mole per mole of iron.

16. The method of claim 9 wherein the concentration of hydroxycarboxylic acid or alkali salt thereof is between 0.05 and 0.16 mole per mole of iron.

17. A method for preparing dextrin-hydroxycarboxylato-polyiron (III) olated complex which comprises, reacting a polyiron (III) olated compound at about 100° C. to 130° C. in the presence of alkali carbonate with dextrin, and then reacting that dextrin-polyiron (III) olated complex with citric acid, gluconic acid, tartaric acid, malic acid or succinic acid or alkali salts thereof at about 100° C. to 130° C., and recovering dextrin-hydroxycarboxylato-polyiron (III) olated complex.

18. A method for preparing dextrin-hydroxycarboxylato-polyiron (III) olated complex which comprises, reacting a polyiron (III) olated compound at about 102° C. to 120° C. for about 1 to 5 hours in the presence of alkali carbonate with about 0.75 to 0.60 moles glucose residue unit per mole of iron of dextrin having an average molecular weight of about 2,500 to 10,000, and then reacting that dextrin-polyiron (III) olated complex with about 0.02 to about 0.20 mole per mole of iron of citric acid, gluconic acid, tartaric acid, malic acid or succinic acid or alkali salts thereof at about 100° C. to 130° C., and recovering dextrin-hydroxycarboxylato-polyiron (III) olated complex.

* * * * *

UNITED STATES PATENT AND TRADEMARK OFFICE
CERTIFICATE OF CORRECTION

PATENT NO. : 4,189,474
DATED : February 19, 1980
INVENTOR(S) : Teikichi Kurosaki et al.

It is certified that error appears in the above-identified patent and that said Letters Patent are hereby corrected as shown below:

Column 16, line 48, delete "$[C_6H_5O_7]$"

Column 16, line 49, delete "$[C_6H_5O_7]$"

Signed and Sealed this

Twenty-ninth Day of July 1980

[SEAL]

Attest:

SIDNEY A. DIAMOND

Attesting Officer

Commissioner of Patents and Trademarks